United States Patent [19]

Toyoda et al.

[11] Patent Number: 5,178,863
[45] Date of Patent: * Jan. 12, 1993

[54] MICROORGANISMS DETOXIFYING FUSARIC ACID AND METHOD FOR DETOXIFYING FUSARIC ACID BY THE USE OF THE SAME

[75] Inventors: Hideyoshi Toyoda, Osaka; Ryutaro Utsumi, Amagasaki, both of Japan

[73] Assignee: Daikin Industries, Ltd., Osaka, Japan

[*] Notice: The portion of the term of this patent subsequent to Jan. 29, 2008 has been disclaimed.

[21] Appl. No.: 648,177

[22] Filed: Jan. 30, 1991

[30] Foreign Application Priority Data

Jan. 31, 1990 [JP] Japan ................................. 2-22957

[51] Int. Cl.$^5$ ..................... A01N 63/00; A01N 25/00; A01N 25/32; C12N 1/20
[52] U.S. Cl. .................. 424/93 D; 435/262; 435/252.1; 435/253.6; 424/405; 424/406
[58] Field of Search ............... 435/262, 264, 267, 243, 435/252.1, 253.6; 424/405, 406, 93 D

[56] References Cited

U.S. PATENT DOCUMENTS 4,761,376  8/1988  Kulpa et al. ..................... 435/264
4,871,673  10/1989  Rehm et al. ..................... 435/264
4,988,586  1/1991  Toyoda et al. ..................... 424/93

FOREIGN PATENT DOCUMENTS 0257756  1/1988  European Pat. Off. .
0251320  3/1988  European Pat. Off. .

OTHER PUBLICATIONS

Chemical Abstracts, vol. 15, p. 222, Abstract No. 117403g, Columbus, Ohio; G. P. Polovinko: "Effect of Gibberellin and Indolylacetic Acid on the Growth and Toxin Production of Cucumber Fusariosis Wilt Agents", 12 Apr. 1982; and Microbiol. ZH (Kiev) 1981, 43(6), 760-4.

Derwent Central Patents Index, Basic Abstracts Journal, Section C, AGDOC, Week 8737, 11th Nov. 1987, Derwent Publications, Ltd., London, GB; & JP-A-62 181 774 (Daikin Kogko K.K.), Oct. 8, 1987.

Primary Examiner—Douglas W. Robinson
Assistant Examiner—Deborah K. Ware
Attorney, Agent, or Firm—Peter J. Dehlinger; Gary R. Fabian

[57] ABSTRACT

A method for the prevention of Fusarium diseases comprising the application of a microorganism that detoxifies fusaric acid to the plant or to the soil. The microorganism is *Klebsiella oxytoca* which has the ability to detoxify fusaric acid.

2 Claims, No Drawings

MICROORGANISMS DETOXIFYING FUSARIC ACID AND METHOD FOR DETOXIFYING FUSARIC ACID BY THE USE OF THE SAME

BACKGROUND OF THE INVENTION

1. Field of the Invention

The present invention relates to microorganisms that have the ability to make fusaric acid (a substance that causes vine-splitting to members of the gourd family, tomato blight or the like) non-toxic to plants, and a method for detoxifying fusaric acid by the use of the microorganisms.

2. Description of the Prior Art

It is known that the genus Fusarium contains species that can cause diseases of wither and blight that can occur during the growth of plants. Diseases such as vine-splitting in members of the gourd family such as cucumbers, watermelons, melons, etc., tomato blight, half-wither disease of eggplants, yellow blight of strawberries, dry rot of devil's foot root, spring blight of grass, etc. are infection of species of Fusarium, named Fusarium oxygsporum fusarium monitiform, Fusarium moniliform, as well as a large number of other species. These fungi contaminate the soil, and are absorbed into the plant from the soil via the xylem. It is thought that the cause of the withering of plants is the fusaric acid that is produced by the metabolism of these fungi. Fusaric acid is produced by almost all species the belong to the genus Fusarium (including the two species mentioned above) that are plant pathogens. This fusaric acid acts as a non-specific toxin, and it damages not only the host plants but also other kinds of plants. Fusaric acid causes an increase in the permeability of plant protoplasmic membranes with respect to tissue fluids that contain $Ca^+$, $K^+$, $Na^+$, or other cations, or that contain various kinds of amino acids, which increase causes exudation of the tissue fluids to surfaces such as those of the leaves of the plant. This exudate dries, and the surfaces of the plants develop high osmotic pressure, which increases the evaporation of water still more. As a result, the plant wilts an dies.

Chemical agents that are used to prevent Fusarium infections include, for example, the o-phenylenediamine derivative include, for example, the o-phenylenediamine derivative with the structure shown below, with the trade name Topjin-M which is used as a soil fungicide.

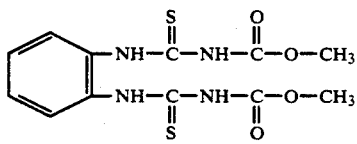

This agent kills the fungi of the genus Fusarium that line in the soil, but if it is merely scattered on the surface of the soil, it is not effective, so it is necessary to mix it into the soil before sowing or planting. This operation requires much labor. There is also the disadvantage that once the symptoms of the infection have appeared, this agent has almost no effect on stopping the progress of the disorder.

There is a variety of tomato that is resistant to infections caused by Fusarium. It has been found that, in the tissues of this variety of tomato, as shown below, fusaric acid (I) is metabolized and decomposed to form N-methylfusaric acid amide (II). The decomposition of fusaric acid is effectively attained among varieties of tomatoes that have strong resistance to Fusarium infections.

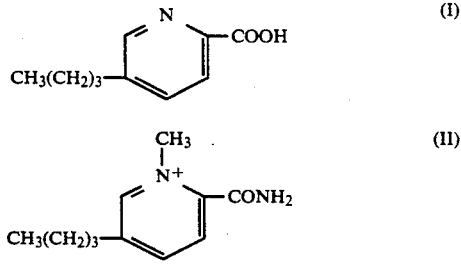

As described above, fusaric acid causes vine-splitting to members of the gourd family, as well as tomato blight or the like. In view of tomatoes having resistance to the above-mentioned infectious diseases, the diseases of plants caused by fusaric acid can be prevented by decomposing or chemically modifying fusaric acid so as to make the fusaric acid non-toxic to plants.

SUMMARY OF THE INVENTION

The microorganisms detoxifying fusaric acid and the method for detoxifying the fusaric acid of this invention, which overcomes the above-discussed and numerous other disadvantages and deficiencies of the prior art, comprises the application of a microorganism which detoxifies fusaric acid to the plant.

A biologically pure culture of microorganism of this invention has the ability to detoxify fusaric acid for plants, wherein the microorganism is Klebsiella oxytoca HY-1 (FERM BP-3221).

The present invention also includes a method for prevention of Fusarium diseases in plants which comprises applying a microorganism capable of detoxifying fusaric acid to the plant or to the soil around the plant, where the microorganism is Klebsiella oxytoca HY-1 (FERM BP-3221).

Thus, the invention described herein makes possible the objectives of (1) providing microorganisms capable of detoxifying fusaric acid produced by the metabolism of species of Fusarium; and (2) providing a method of detoxifying fusaric acid by the use of the above-mentioned microorganisms.

DESCRIPTION OF THE PREFERRED EMBODIMENTS

The microorganisms of the present invention are bacteria belonging to the genus Klebsiella. Preferably, they are Klebsiella oxytoca, and especially, the Klebsiella oxytoca HY-1 strain obtained from the soil of Higashi-Osaka City, Japan is more preferred. The microorganisms of the present invention is non-pathogenic to plants. The above-mentioned Klebsiella oxytoca HY-1 strain was identified by Bergey's Manual of Systematic Bacteriology Volume 1 on the basis of the bacteriological characteristics described below. This strain is characteristic of its ability to detoxify fusaric acid.

Bacteriological Characteristics

The Morphology, growth on different media, physiological characteristics and other characteristics of Klebsiella oxytoca HY-1 strain of the present invention are shown in Table 1.

TABLE 1

| Bacteriological characteristics | |
|---|---|
| (a) Morphology | |
| ① Shape and size of cells | Short rods (0.3–1.0) × (1.0–4.0) μm |
| ② Polymorphism | None |
| ③ Mobility | None |
| ④ Spore | None |
| ⑤ Gram staining | Negative |
| ⑥ Acid fastness | None |
| (b) Growth on different media | |
| ① Nutrient broth agar plate culture | |
| Growth | Abundant growth |
| Colony edge | Entire |
| Colony surface | Smooth |
| Glossiness of colony | Glistening |
| State of colony | Butyrous |
| Color | Light yellow |
| ② Nutrient broth agar slant culture | |
| Growth | Abundant growth |
| Colony surface | Smooth |
| Glossiness of colony | Glistening |
| State of colony | Butyrous |
| Color | Light yellow |
| ③ Nutrient broth liquid culture | Strongly turbidic Ring formation |
| ④ Nutrient broth gelatin stab culture | No liquefaction Gas generated inside |
| ⑤ Litmusmilk | Acid Coagulation No peptonization |
| (c) Physiological characteristics | |
| ① Nitrate reduction | + |
| ② Denitrification | + |
| ③ MR test | − |
| ④ VP test | − |
| ⑤ Indole production | + |
| ⑥ Hydrogen sulfide production | − |
| ⑦ Starch hydrolysis | − |
| ⑧ Utilization of citric acid | + |
| ⑨ Utilization of inorganic nitrogen source | |
| Nitrate | − |
| Ammonium salt | − |
| 10 Production of pigments | |
| King A medium | Diffusible pigment and fluorescent pigment were not produced. |
| King B medium | Diffusible pigment and fluorescent pigment were not produced. |
| Pseudomonas F medium | Diffusible pigment and fluorescent pigment were not produced. |
| Pseudomonas P medium | Diffusible pigment and fluorescent pigment were not produced. |
| 11 Crease | + |
| 12 Oxidase | − |
| 13 Catalase | + |
| 14 Growth limits | |
| pH | 4.5–9.5 |
| Optimum pH | 6.0–8.5 |
| Temperature | 9–45° C. |
| 15 Oxygen requirement | Facultatively aerobic |
| 16 O-F test | |
| D-Glucose | Fermentation |
| D-Sorbitol | Fermentation |
| Sucrose | Fermentation |
| Lactose | Fermentation |
| L-Arabinose | Fermentation |
| 17 Production of acid and gas | (Production of acid) (Production of gas) |

TABLE 1-continued

| Bacteriological characteristics | | |
|---|---|---|
| ① L-Arabinose | + | − |
| ② D-Xylose | + | − |
| ③ D-Glucose | + | − |
| ④ D-Mannose | + | − |
| ⑤ D-Fructose | + | + |
| ⑥ D-Galactose | + | + |
| ⑦ Maltose | + | + |
| ⑧ Sucrose | + | + |
| ⑨ Lactose | + | + |
| 10 Trehalose | + | + |
| 11 D-Sorbitol | + | + |
| 12 D-Mannitol | + | + |
| 13 Inositol | + | + |
| 14 Glycerol | + | + |
| 15 Starch | − | − |
| (d) Other characteristics | | |
| ① Esculin decomposition | + | |
| ② Use of Malonic acid | ± | |
| ③ Arginine decomposition | − | |
| ④ Lysine decarboxylation | + | |
| ⑤ Ornithine decarboxylation | − | |
| ⑥ Phenylalanine deaminatino | − | |
| ⑦ Lipase | − | |
| ⑧ Auxotrophy | None | |
| ⑨ DNase | − | |

Identification of Strain

From the above-mentioned bacteriological characteristics, this strain was identified as above and designated as *Klebsiella oxytoca* HY-1 strain. This strain was deposited with the Fermentation Research Institute, Agency of Industrial Science and Technology, 1-3, Higashi 1-chome, Tsukuba-shi, Ibaraki-ken, Japan, under Accession No. FERM BP-3221, where it will be maintained under the terms of the Budapest Treaty.

Culture Conditions

Special medium is not needed. To a minimal medium that contains phosphate, sulfate, chloride, etc., with potassium, sodium, magnesium, etc., sugars such as glucose, sucrose, etc., casamino acid, etc., can be added as the carbon source. As the nitrogen source to be used in this minimal medium, inorganic nitrogen such as nitrate, ammonium salt, and/or organic nitrogen with amino groups can be added. As the source nutrients, it is possible to add corn steep liquor, yeast extract, etc., as need. The temperature of culture can be 10°–45° C., and preferably around 37° C. The culture pH can be 4.5–9.5, and preferably 6.0–8.0. Culture is maintained for 1 to 5 days aerobically, with agitation or oscillation. Solid culture (agar medium) can also be possibly used.

Detoxification of Fusaric Acid

When the microorganism of this invention is grown in the appropriate medium described above, and at least one selected from the group consisting of cells of the microorganism their culture fluid, their cell homogenates and their cell extracts is brought into contact with fusaric acid, the fusaric acid is made non-toxic to plants. Such an ability of detoxifying fusaric acid, owned by the microorganisms of the present invention, is caused by the decomposition and/or chemical modification of fusaric acid. The microorganisms of the present invention are used for preventing plant diseases caused by species of Fusarium. For example, since fusaric acid can be detoxified by the method of scattering at least one selected from the group consisting of microorganisms of the present invention, their cells, their culture fluid, their cell homogenates and their cell extracts to plants, the method of spraying them onto plants, so it will adhere them onto the surface of plants, and the method of inserting them into the soil, it is possible to prevent diseases caused by fusaric acid.

EXAMPLE

Hereinafter, the present invention will be described by illustrating the examples.

EXAMPLE 1

Soil obtained in the Kowakae area of Higashi-Osaka City, Japan, was suspended in sterilized water, and the supernatant obtained was diluted, spread onto the screening medium (containing fusaric acid) described in Table 2, and then cultured for 48 hours at 30° C.

TABLE 2

| Medium composition | | |
|---|---|---|
| | $Na_2HPO_4$ | 7 g |
| | $KH_2PO_4$ | 3 g |
| | NaCl | 0.5 g |
| Inorganic salt | $NH_4Cl$ | 1 g |
| | $CaCl_2$ | 0.1 g |
| | $MgSO_4$ | 1 g |
| | Casamino acid | 4 g |
| | Fusacric acid | 100 mg |
| | Water | 1 l |
| | (pH 7.2 in medium) | |

After culture, a strain which is a short rod without flagellum and has the ability of sugar fermentation was isolated from the resultant colony. The isolated strain was inoculated again onto the same medium, and the resultant species were identified by their bacteriological characteristics shown in Table 1. This train was identified as *Klebsiella oxytoca* HY-1 strain.

EXAMPLE 2

A suspension of *Klebsiella oxytoca* HY-1 strain obtained in Example 1 was made with cells at a concentration of $10^9$/ml in pure water. Pure water was used as the control. Two groups of tomatoes in the fifth to sixth internodal growth period, each group containing five tomato cuttings, were used. The cutting ends of the tomatoes were submerged for 3 hours in the suspension mentioned above and water for the test and the control groups, respectively. Then the cutting ends were washed with water, and inserted into about 20 ml of an aqueous solution of fusaric acid at a concentration of 300 μg/ml until 10 ml of the solution had been absorbed. Then the cutting ends were washed with water and the cutting ends were inserted in water and kept at 20° C.

When the water control was used, symptoms of withering of all of the leaves were observed 8 to 16 hours after the beginning of the soaking in the aqueous solution of fusaric acid, and the stems and veins of the leaves turned brown and died. When the suspension of the HY-1 strain was used, no symptoms were found in any of the five cuttings 72 hours later.

EXAMPLE 3

*Klebsiella oxytoca* HY-1 strain obtained in Example 1 was cultured in the medium (containing fusaric acid) described in Table 2. A portion of the culture fluid was taken at 0, 24, 48, and 72 hours after the start of culture. Each portion was centrifuged for 10 minutes at 3000 G to obtain a supernatant, which was filtered through a membrane filter with 0.2 μm pores. The filtrate obtained and Murashiga-Skoog (MS) medium (Physiol. Plants. 15, 473 (1962)) were mixed at the volume ratio of 1:9. Then callus induced from the cambium of tomato (*Lycopersicon esculentym* Mill cv. Zuiko) was added to the mixture to the concentration of $10^4$ and $10^5$ cells per milliliter of medium and left for 24 hours at 25° C. Then the callus cells were stained with fluorescein diacetate (FDA). The stained cells were observed under a fluorescence microscope, and the percentage of callus cells that had survived was calculated (n=500). As a control, MS medium was used instead of the mixture mentioned above. The results are shown in Table 3.

TABLE 3

| | Surviving tomato callus cells (%) |
|---|---|
| Control | 87.0 |
| At start | 0.4 |
| 24 hr later | 46.7 |
| 48 hr later | 65.2 |
| 72 hr later | 85.8 |

According to the present invention, as described above, the species of Klebsiella capable of detoxifying fusaric acid is provided. When applying at least one of the group consisting of microorganisms, their cells, their culture fluid, their cell homogenates and their cell extracts to the soil or plants, even though the soil or plants are infected with various species of Fusarium, fusaric acid produced by the species of Fusarium is detoxified. Accordingly, diseases such as vine-splitting and blight caused by the infection of Fusarium do not occur. Also, when applied to the plants and soil on which infections diseases have already occurred, since fusaric acid is detoxified, the advancement of the infectious diseases can be prevented.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A biologically pure culture consisting of a microorganism having the ability to detoxify fusaric acid for plants, wherein said microorganism is *Klebsiella oxytoca* HY-1 (FERM BP-3221).

2. A method for the prevention of Fusarium diseases in a plant, comprising
   applying a microorganism capable of detoxifying fusaric acid to said plant or to the soil around said plant, wherein said microorganism is *Klebsiella oxytoca* HY-1 (FERM BP-3221).

* * * * *

UNITED STATES PATENT AND TRADEMARK OFFICE
CERTIFICATE OF CORRECTION

PATENT NO. : 5,178,863

DATED : January 12, 1993

INVENTOR(S) : H. Toyoda and R. Utsumi

It is certified that error appears in the above-indentified patent and that said Letters Patent is hereby corrected as shown below:

Column 1, line 22, after "grass, etc. are" insert --caused by the--.
Column 1, line 23 delete "fusarium moniliform" (first occurrence).
Column 1, line 29, after "almost all species" delete "the and insert --that--.
Column 1, line 36, delete "CA$^+$" and insert --CA$^{2+}$--.
Column 1, line 42, after "the plant wilts" delete "an" and insert --and--.
Column 1, line 56, delete "line" and insert --live--.
Column 2, line 58, delete "is" and insert --are--.
Column 3, in TABLE 1, [2nd column thereof], line 36 [opposite column 1 entry reading "VP test," delete the minus symbol and insert plus symbol (--+--).
Column 3, in TABLE 1, [2nd column thereof], line 43 [opposite column 1 entry reading "Nitrate," delete the minus symbol and insert plus symbol (--+--).
Column 3, in TABLE 1, [2nd column thereof], line 44 [opposite column 1 entry reading "Ammonium salt," delete the minus symbol and insert plus symbol (--+--).
Column 3, in TABLE 1, line 55, after "11" delete "Crease" and insert --Urease--.
Column 3, in TABLE 1, line 61, after "Facultatively" delete "aerobic" and insert --anaerobic--.

UNITED STATES PATENT AND TRADEMARK OFFICE
CERTIFICATE OF CORRECTION

PATENT NO. : 5,178,863
DATED : January 12, 1993
INVENTOR(S) : H. Toyoda and R. Utsumi It is certified that error appears in the above-indentified patent and that said Letters Patent is hereby corrected as shown below:

Column 4, in TABLE 1-continued [3rd column thereof], approximately lines 4-8 [opposite each of the column 1 entries reading "L-Arabinose," "D-Zylose," "D-Glucose," and "D-Mannose"], delete minus symbol and insert plus symbol (--+--).

Column 4, in TABLE 1-continued [1st column thereof], line 26, insert --ONPG (β-Galactosidase-- and on the same line, in the second column of the Table, insert the plus symbol (--+--).

Column 4, line 59, after "microorganism" add a comma (,).
Column 5, in TABLE 2, line 27, delete "Fusacric" and insert --Fusaric--.
Column 6, line 9, delete "esculentym" and insert --esculentum--.
Column 6, line 39, delete "infections" and insert --infectious--.

Signed and Sealed this

Twenty-fifth Day of April, 1995

Attest:

BRUCE LEHMAN

Attesting Officer     Commissioner of Patents and Trademarks